United States Patent [19]

Meyer et al.

[11] 4,016,277

[45] Apr. 5, 1977

[54] 4-QUINOLINE AND 4-ISOQUINOLINE DERIVATIVES OF 2,6-DIAMINO-1,4-DIHYDROPYRIDINE

[75] Inventors: Horst Meyer, Wuppertal; Friedrich Bossert, Wuppertal-Elberfeld; Wulf Vater, Opladen; Kurt Stoepel, Wuppertal, all of Germany

[73] Assignee: Bayer Aktiengesellschaft, Germany

[22] Filed: Feb. 28, 1975

[21] Appl. No.: 554,135

Related U.S. Application Data

[60] Division of Ser. Nos. 454,996, March 27, 1974, Pat. No. 3,950,336, and Ser. No. 445,258, March 27, 1974, Pat. No. 3,905,747, each is a division of Ser. No. 336,483, Feb. 28, 1973, Pat. No. 3,855,231.

[30] Foreign Application Priority Data

Mar. 6, 1972  Germany .......................... 2210687

[52] U.S. Cl. .......................... 424/258; 260/287 D; 260/287 CE
[51] Int. Cl.$^2$ ......................................... A61K 31/47
[58] Field of Search ............. 260/287 CE; 424/258

[56] References Cited

UNITED STATES PATENTS 2,359,329  10/1944  Phillips et al. ............... 260/287 CE

OTHER PUBLICATIONS

Harington, "Hypotensive Drugs", 1956, pp. 8, 9, 13, 35–37, 74–75, 82, 92–93, 124, 125, 193–195.
Donoso, "Drugs in Cardiology," vol. I parts 1 and 2, 1975, (1) pp. 1–2, 12, 13, 16, 70–71, (2) 1, 12, 18–19, 31, 34.
McMahon, "Cardiovascular Drugs," 1975, pp. 1–3, 22–23, 121–122.

*Primary Examiner*—Donald G. Daus
*Assistant Examiner*—David E. Wheeler

[57] ABSTRACT

2,6-Diamino-1,4-dihydropyridines bearing carbonyl functions in the 3- and 5-positions and being substituted in the 4-position by lower alkyl, phenyl, substituted phenyl or a heterocyclic group are antihypertensive agents and coronary vessel dilators. The compounds, of which 2,6-diamino-4-(3-nitrophenyl)-1,4-dihydropyridine-3,5-dicarboxylic acid 3,5-diethyl ester is a representative embodiment, are prepared through condensation of an amidine with either an aldehyde or an ylidenecyanoacetoacetic acid ester.

8 Claims, No Drawings

4-QUINOLINE AND 4-ISOQUINOLINE DERIVATIVES OF 2,6-DIAMINO-1,4-DIHYDROPYRIDINE

This is a division of application Ser. No. 454,996, now U.S. Pat. No. 3,950,336, and Ser. No. 445,258, now U.S. Pat. No. 3,905,747, both filed Mar. 27, 1974, which in turn are divisional applications of Ser. No. 336,483, filed Feb. 28, 1973, now U.S. Pat. No. 3,855,231.

DETAILED DESCRIPTION

The present invention pertains to 2,6-diamino-1,4-dihydropyridine derivatives, to process for their production and use and to pharmaceutical compositions containing such compounds and useful as antihypertensive agents and coronary vessel dilators.

In particular, the present invention pertains to compounds of the formula:

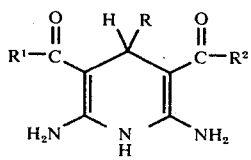

wherein
R is hydrogen; lower alkyl; lower alkenyl; lower alkynyl, phenyl; substituted phenyl in which the substituents are one to three members selected from the group consisting of lower alkyl, lower alkoxy, halogeno, nitro, cyano, trifluoromethyl, azido, carbo(lower alkoxy), lower alkylsulfonyl, lower alkylsulfinyl, lower alkylthio or phenyl; naphthyl; or a heterocyclic ring selected from the group consisting of quinolyl, isoquinolyl, pyridyl, pyrimidyl, thenyl, furyl and pyrryl, said heterocyclic ring being unsubstituted or substituted by one or two members selected from the group consisting of lower alkyl, lower alkoxy and halogeno; and each of $R^1$ and $R^2$, taken independently of the other, is lower alkyl, lower alkoxy, lower alkoxy(lower alkoxy), lower alkenyloxy, lower alkynyloxy, amino, lower alkylamino or di(lower alkyl) amino.

The above compounds can be depicted in tautomeric forms, all of which are fully equivalent and fully embraced by the present invention:

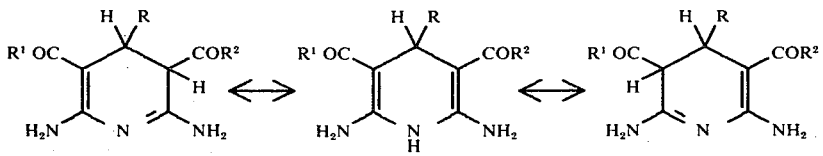

For the sake of brevity and convenience, the 1,4-dihydro form is employed herein.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec. butyl, tert. butyl, pentyl, isopentyl, neopentyl, tert. pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term lower alkynyl denotes a univalent branched or straight hydrocarbon chain containing from 2 to 6 carbon atoms and nonterminal acetylenic unsaturation as, for example, ethynyl, 2-propynyl, 4-pentynyl, and the like.

The term lower alkoxy denotes a straight or branched hydrocarbon chain bound to the remainder of the molecule through an ethereal oxygen atom as, for example, methoxy, ethoxy, propoxy, isopropoxy, butoxy, isobutoxy, pentoxy and hexoxy.

The term lower alkylthio denotes a branched or straight hydrocarbon chain bound to the remainder of the molecule through a divalent sulfur as, for example, methylthio, ethylthio, propylthio, isopropylthio, butylthio, and the like.

The term halogen denotes the substituents fluro, chloro, bromo and iodo.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

According to the present invention, the foregoing compounds are prepared by reacting an amidine of the formula:

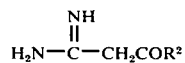

wherein $R^2$ is as herein defined, with either (a) an aldehyde of the formula RCHO wherein R is as herein defined, or (b) with an ylidenecyanoacetic acid derivative of the formula:

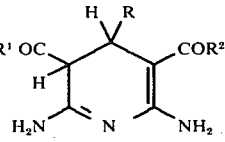

in which R and $R^1$ are as herein defined in the presence of an alkali metal alkoxide such as sodium methoxide.

The condensations proceed smoothly in good yields simply by heating the two components, generally in the presence of an inert organic solvent such as methanol, ethanol, propanol and similar alkanols, ethers such as dioxane and diethyl ether, glacial acetic acid, pyridine, dimethylformamide, dimethylsulfoxide, acetonitrile, and the like. The reactions are conducted at temperatures of from 20° to 200° C, conveniently at the boiling point of the solvent, and while elevated pressure may be utilized, normal atmospheric pressure is generally satisfactory. The reactants are employed in substantially equimolar amounts when the amidine is reacted with the ylidenecyanoacetic acid whereas at least two molar equivalents of the amidine are employed per molar equivalent of the aldehyde reactant, in which case $R^1$ and $R^2$ are the same in the dihydropyridine product. The amidine reactant can be employed as the free base or in the form of a salt such as the hydrohalide salts with the amidine being liberated from the salt through treatment wit a basic agent such as an alkali metal alkoxide.

It is rather surprising that the above described condensations produce the desired compounds in such good yields ad with such high purity. Thus the water formed in the initial condensationof the aldehyde and amidine could be expected to hydrolyze the resultant ylideneamidine wit formation of an lylideneamide. Moreover, while it is known that a benzzylideneacetoacetic acid ester can be condensed with an amino crotonic acid ester to yield a 1,4-dihydropyridine (Knoevenagel, Ber. 31, 743, 1898), it would be expected from, for example, Silversmith, J. Org. Chem. 27, 4090 (1952) that the addition of the amidine to the ylideneamidine or the ylidenecyanoacetic would yield the dihydropyrimidine derivative rather than the dihydropyridine derivative.

Many of the aldehydes utilized as one of the reactants are known to the art and the others can either be generated in situ as herein described or prepared according to methods well known to the art, see for example Org. Reactions VIII, 218 et seq. (1954). Typical of this reactant are the following compounds:
  formaldehyde,
  acetaldehyde,
  propionaldehyde,
  isobutyraldehyde,
  cyclopentaldehyde,
  cyclohexanaldehyde,
  acrolein,
  cyclohex-3-enaldehyde,
  benzaldehyde,
  2-, 3- and 4-methylbenzaldehyde,
  2-, 3- and 4-methoxybenzaldehyde,
  3,4 and 5-trimethoxybenzaldehyde,
  2-isopropoxybenzaldehyde,
  2-, 3- and 4-chlorobenzaldehyde,
  2-, 3- and 4-bromobenzaldehyde,
  2-, 3- and 4-fluorobenzaldehyde,
  2,4- and 2,6-dichlorobenzaldehyde,
  2,4- and 2,3-dimethylbenzaldehyde,
  2-, 3- and 4-nitrobenzaldehyde,
  2,6- and 3,5-dinitrobenzaldehyde,
  2-nitro-6-bromobenzaldehyde,
  2-nitro-3-methoxy-6-chlorobenzaldehyde,
  2-nitro-4-chlorobenzaldehyde,
  2-nitro-4-methoxybenzaldehyde,
  2-, 3- and 4-trifluoromethylbenzaldehyde,
  2-carbethoxybenzaldehyde,
  3-carbomethoxybenzaldehyde,
  4-carbobutoxybenzaldehyde,
  3-nitro-4-carbethoxybenzaldehyde-4-carboxylic acid ethyl ester,
  $\alpha,\beta$- and $\gamma$-pyridinaldehyde,
  6-methylpyridin-2-aldehyde,
  pyrimidin-5-aldehyde,
  4,6-dimethoxypyrimidin-5-aldehyde,
  2-, 3- and 4-cyanobenzaldehyde,
  2-methylmercaptobenzaldehyde,
  4-methylmercaptobenzaldehyde,
  2-methylsulphonylbenzaldehyde,
  1- and 2-naphthaldehyde,
  5-bromo-1-naphthaldehyde,
  2-ethoxy-1-naphthaldehyde,
  4-methyl-1-naphthaldehyde,
  quinolin-2-, 3-, 4-, 5-, 6-, 7- and 8-aldehyde,
  isoquinolin-1,3,4-aldehyde,
  furan-2-aldehyde,
  thiophen-2-aldehyde and
  pyrrol-2-aldehyde.

The ylidenecyanoacetic acid reactants are similarly known or can be readily produced according to known methods, see for example Newman et al., J. Org. Chem., 23, 797 (1958). Typical of these reactants are the following
  benzylidenecyanoacetic acid methyl ester,
  benzylidenecyanoacetic acid ethyl ester,
  benzylidenecyanoacetic acid propargyl ester,
  benzylidenecyanoacetic acid $\beta$-methoxyethyl ester,
  1-naphthylidenecyanoacetic acid ethyl ester,
  2-methoxybenzylidenecyanoacetic acid ethyl ester,
  2-methylbenzylidenecyanoacetic acid ethyl ester,
  2-nitrobenzylidenecyanoacetic acid isopropyl ester,
  2-trifluoromethylbenzylidenecyanoacetic acid ethyl ester,
  2-cyanobenzylidenecyanoacetic acid methyl ester,
  2-chlorobenzylidenecyanoacetic acid propyl ester,
  4-methylmercaptobenzylidenecyanoacetic acid ethyl ester,
  $\alpha$-pyridylmethylidenecyanoacetic acid ethyl ester, and
  2-furfurylidenecyanoacetic acid ethyl ester.

The amidine reactants are similarly known or can be readily produced according to known methods, see for example McElvain et al., J.A.C.S., 73, 2760 (1951). Typical of these reactants are the following:
  amidinoacetic acid methyl ester,
  amidinoacetic acid ethyl ester,
  amidinoacetic acid n-propyl ester,
  amidinoacetic acid isopropyl ester,
  amidinoacetic acid cyclohexyl ester,
  amidinoacetic acid $\beta$-methoxyethyl ester,
  amidinoacetic acid $\alpha$-ethoxyethyl ester,
  amidinoacetic acid $\beta$-ethoxyethyl ester,
  amidinoacetic acid propargyl ester,
  amidinoacetamide, and
  amidino-N,N-dimethylacetamide.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilation of the coronary vessels which is intensified by a simultaneous nitrite-like effect of reducing the load on the heart. The effect on heart metabolism is thus one of energy saving. In addition, the compounds lower the blood pressure of normotonic and hypertonic animals and can thus be used as antihypertensive agents. These properties can be conveniently observed in well known laboratory models. Thus for example the coronary vessel dilation effect can be observed by measuring the increase in oxygen saturation in the coronary sinus in the narcotized, heart catheterized dog, as shown in the following table:

| Compound | I.V. Dose (mg/kg) | ΔO₂ % saturation | Return to normal O₂ values (hours) |
|---|---|---|---|
| 2,6-diamino-4-(2-nitrophenyl)-1,4-dihydropyridine-3,5-dicarboxylic acid 3,5-diethyl ester | 0.3 | 26 | 2 |
| 2,6-diamino-4-(3-nitrophenyl)-1,4-dihydropyridine-3,5-dicarboxylic acid diethyl ester | 0.2 | 26 | 2 |

The hypotensive activity of the present compounds can be observed by measuring the blood pressre of hypertensive rats following administration of the compounds. The following table demonstrates the dose which results in at least a 15 mm Hg reduction in blood pressure of such animals:

| Compound | Dose (mg/kg) |
|---|---|
| 2,6-diamino-4-(2-methylphenyl)-1,4-dihydropyridine-3,5-dicarboxylic acid diethyl ester | 10.0 |
| 2,6-diamino-4-(2-nitrophenyl)-1,4-dihydropyridine-3,5-dicarboxylic acid 3,5-diethyl ester | 1.0 |
| 2,6-diamino-4-(2-methoxyphenyl)-1,4-dihydropyridine-3,5-dicarboxylic acid diethyl ester | 10.0 |
| 2,6-diamino-4-(2-cyanophenyl)-1,4-dihydropyridine-3,5-dicarboxylic acid diethyl ester | 0.3 |
| 2,6-diamino-4-(3-nitrophenyl)-1,4-dihydropyridine-3,5-dicarboxylic acid diethyl ester | 1.0 |

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. This vascular-spasmolytic action can be observed in the entire vascular system as well as in more or less isolated and circumscribed vascular regions such as the central nervous system. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 95 to 0.5%, of at least one 2,6-diamino-1,4-dihydropyridine as herein defined in combination with a pharmaceutical carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 0.5 to about 1800 mg/kg, preferably 2.5 to 900 mg/kg, when administered parenterally and from about 25 to about 4500 mg/kg, preferably 50 to 1800 mg/kg, when administered orally. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solution, and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated by example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax, or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to adminstration. Non-toxic salts and salt solutions can be added to render the injection isotonic. Stabilizers, preservatives and emulsifiers can also be added.

The following examples will serve to further typify the nature of the present invention through the presentation of specific embodiments. These examples should not be construed as a limitation on the scope of the invention since the subject matter regarded as the invention is set forth in the appended claims.

EXAMPLE 1

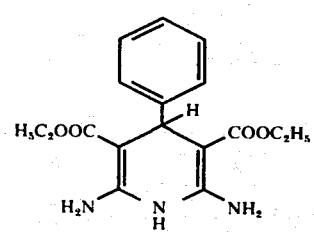

Upon boiling a solution of 5.3 g benzaldehyde and 13.0 g amidinoacetic acid ethyl ester in 150 ml ethanol for two hours, 2,6-diamino-4-phenyl-1,4-dihydropyridine-3,5-dicarboxylic acid diethyl ester of m.p. 139° C (isopropanol) is obtained.

Yield: 59% of theory.

EXAMPLE 2

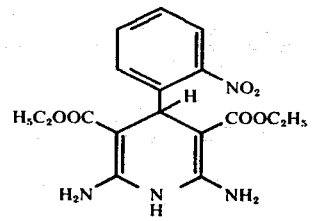

Upon boiling a solution of 7.6 g 2-nitrobenzaldehyde and 13.0 g amidinoacetic acid ethyl ester in 150 ml ethanol for two hours, 2,6-diamino-4-(2-nitrophenyl)-1,4-dihydropyridine-3,5-dicarboxylic acid diethyl ester of m.p. 142° C (ethanol) is obtained.

Yield: 56% of theory.

EXAMPLE 3

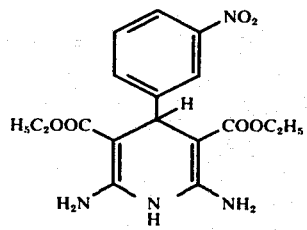

Upon boiling a solution of 15.1 g 3-nitrobenzaldehyde and 26.0 g amidinoacetic acid ethyl ester in 250 ml ethanol for two hours, 2,6-diamino-4-(3-nitrophenyl)-1,4-dihydropyridine-3,5-dicarboxylic acid diethyl ester of m.p. 175° – 176° C (ethanol) is obtained.

Yield: 63% of theory.

EXAMPLE 4

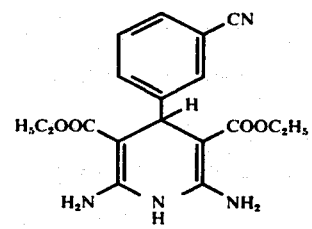

Upon boiling a solution of 6.5 g 3-cyanobenzaldehyde and 13.0 amidinoacetic acid ethyl ester in 150 ml ethanol for two hours, 2,6-diamino-4-(3-cyanophenyl)-1,4-dihydropyridine-3,5-dicarboxylic acid diethyl ester of m.p. 176° C (isopropanol) is obtained.

Yield: 55% of theory.

EXAMPLE 5

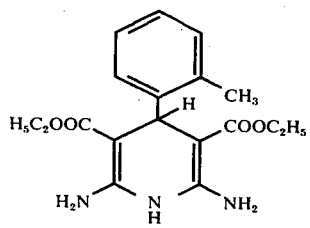

Upon boiling a solution of 6.0 g 2-methylbenzaldehyde and 13.0 g amidinoacetic acid ethyl ester in 150 ml ethanol for two hours, 2,6-diamino-4-(2-methylphenyl)-1,4-dihydropyridine-3,5-dicarboxylic acid diethyl ester of m.p. 158° C (ethanol) is obtained.

Yield: 67% of theory.

EXAMPLE 6

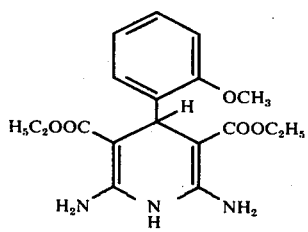

Upon boiling a solution of 6.8 g 2-methoxybenzaldehyde and 13.0 g amidinoacetic acid ethyl ester in 150 ml ethanol for two hours, 2,6-diamino-4-(2-methoxyphenyl)-1,4-dihydropyridine-3,5-dicarboxylic acid diethyl ester of m.p. 147° C (ethanol) is obtained.

Yield: 72% of theory.

EXAMPLE 7

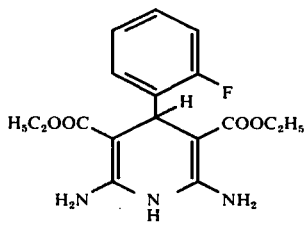

Upon boiling a solution of 6.2 g 2-fluorobenzaldehyde and 13.0 g amidinoacetic acid ethyl ester in 150 ml ethanol for one hour, 2,6-diamino-4-(2-fluorophenyl)-1,4-dihydropyridine-3,5-dicarboxylic acid diethyl ester of m.p. 128°–130° C (ethanol) is obtained).

Yield: 49% of theory.

EXAMPLE 8

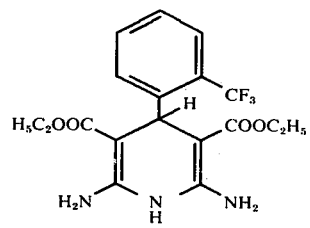

Upon boiling a solution of 8.7 g 2-trifluoromethylbenzaldehyde and 13.0 g amidinoacetic acid ethyl ester in 150 ml of ethanol for two hours, 2,6-diamino-4-(2-trifluoromethylphenyl)-1,4-dihydropyridine-3,5-dicarboxylic acid diethyl ester of m.p. 191° C (ethanol) is obtained.

Yield: 70% of theory.

EXAMPLE 9

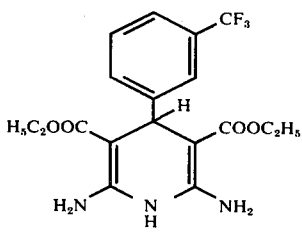

Upon heating a solution of 8.7 g 3-trifluoromethylbenzaldehyde and 13.0 g amidinoacetic acid ethyl ester in 150 ml ethanol for one hour, 2,6-diamino-4-(3-trifluoromethylphenyl)-1,4-dihydropyridine-3,5-dicarboxylic acid diethyl ester of m.p. 170° C (isopropanol) is obtained.

Yield: 56% of theory.

EXAMPLE 10

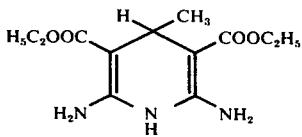

Upon boiling a solution of 5.0 g acetaldehyde and 2.60 g amidinoacetic acid ethyl ester in 150 ml ethanol for two hours, 2,6-diamino-4-methyl-1,4-dihydropyridine-3,5-dicarboxylic acid diethyl ester of m.p. 136° C (ethyl acetate/petroleum ether) is obtained.

Yield: 61% of theory.

EXAMPLE 11

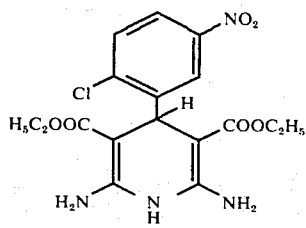

Upon boiling a solution of 9.3 g 3-nitro-6-chlorobenzaldehyde and 13.0 g amidinoacetic acid ethyl ester in 150 ml ethanol for two hours, 2,6-diamino-4-(3-nitro-6-chlorophenyl)-1,4-dihydropyridine-3,5-dicarboxylic acid diethyl ester of m.p. 130° C (ethanol) is obtained.

Yield: 48% of theory.

EXAMPLE 12

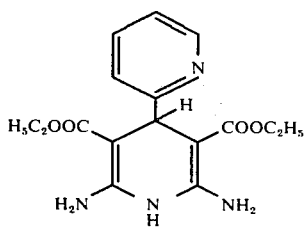

Upon heating a solution of 5.4 g α-pyridinaldehyde and 13.0 g amidinoacetic acid ethyl ester in 150 ml ethanol for two hours, 2,6-diamino-4-(α-pyridyl)-1,4-dihydropyridine3,5-dicarboxylic acid diethyl ester of m.p. 180° C (ethanol) is obtained.

Yield: 74% of theory.

EXAMPLE 13

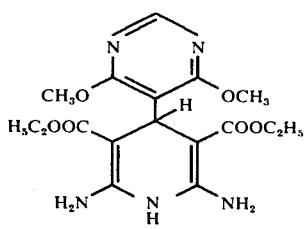

Upon heating a solution of 8.4 g 4,6-dimethoxypyrimidine-5-aldehyde and 13.0 g amidinoacetic acid ethyl ester in 150 ml ethanol for two hours, 2,6-diamino-4-(4,6-dimethoxypyrimid-5-yl)-1,4-dihydropyridine-3,5-dicarboxylic acid diethyl ester of m.p. 219° C (ethanol) is obtained.

Yield: 56% of theory.

EXAMPLE 14

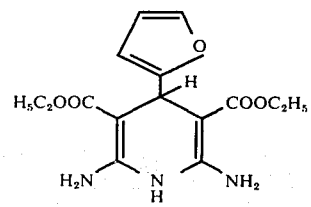

Upon boiling a solution of 4.8 g furan-2-aldehyde and 13.0 g amidinoacetic acid ethyl ester in 150 ml ethanol for two hours, 2,6-diamino-4-(furyl-2)-1,4-dihydropyridine-3,5-dicarboxylic acid diethyl ester of m.p. 147° – 148° C (ethanol) is obtained.

Yield: 74% of theory.

EXAMPLE 15

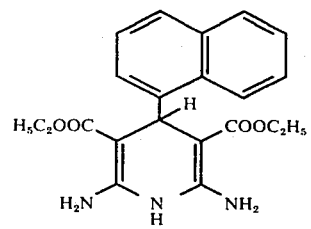

Upon boiling a solution of 7.8 g 1-naphthaldehyde and 13.0 g amidinoacetic acid ethyl ester in 150 ml ethanol for two hours, 2,6-diamino-4-(naphth-1-yl)-1,4-dihydropyridine-3,5-dicarboxylic acid diethyl ester of m.p. 162° – 163° C (ethanol) is obtained.

Yield: 52% of theory.

EXAMPLE 16

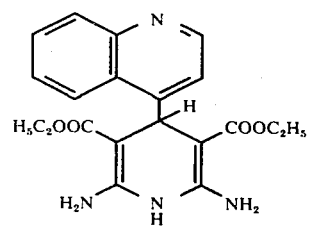

Upon heating a solution of 7.8 g quinoline-4-aldehyde and 13.0 g amidinoacetic acid ethyl ester in 200 ml ethanol for two hours, 2,6-diamino-4-(quinol-4-yl)-1,4-dihydropyridine-3,5-dicarboxylic acid diethyl ester of m.p. 145° (ethanol) is obtained.

Yield: 58% of theory.

EXAMPLE 17

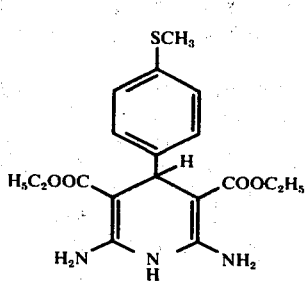

Upon heating a solution of 7.6 g 4-methylmercaptobenzaldehyde and 13.0 g amidinoacetic acid ethyl ester in 200 ml ethanol for two hours, 2,6-diamino-4-(4-methylmercaptophenyl)-1,4-dihydropyridine-3,5-dicarboxylic acid diethyl ester of m.p. 127° C (isopropanol) is obtained.

Yield: 48% of theory.

EXAMPLE 18

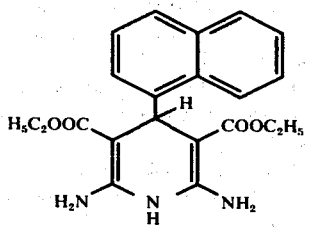

Upon heating a solution of 9.1 g biphenyl-2-aldehyde and 13.0 g amidinoacetic acid ethyl ester in 200 ml ethanol for two hours, 2,6-diamino-4-(biphenyl-2-yl)-1,4-dihydropyridine-3,5-dicarboxylic acid diethyl ester of m.p. 215° (ethanol) is obtained.

Yield: 33% of theory.

EXAMPLE 19

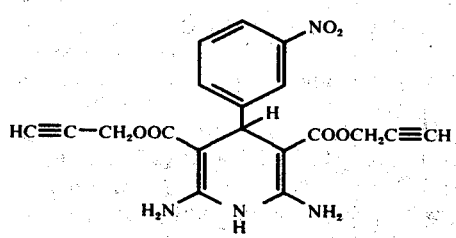

Upon heating a solution of 7.6 g nitrobenzaldehyde and 14.0 g amidinoacetic acid propargyl ester in 200 ml ethanol for two hours, 2,6-diamino-4-(3-nitrophenyl)-1,4-dihydropyridine-3,5-dicarboxylic acid dipropargyl ester of m.p. 170° (ethanol) is obtained.

Yield: 59% of theory.

EXAMPLE 20

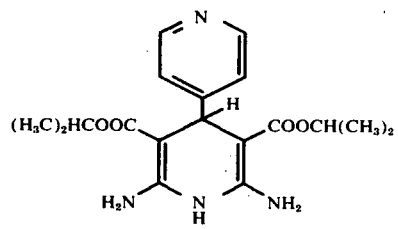

Upon heating a solution of 5.4 g pyridine-4-aldehyde and 14.4 g amidinoacetic acid isopropyl ester in 200 ml of ethanol, 2,6-diamino-4-(pyrid-4-yl)-1,4-dihydropyridine-3,5-dicarboxylic acid diisopropyl ester of m.p. 263° C (ethanol) is obtained.

Yield: 76% of theory.

EXAMPLE 21

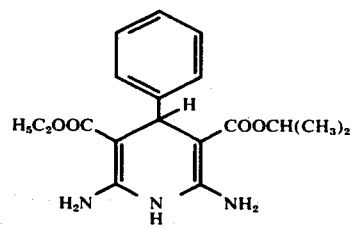

Upon heating a solution of 10.1 g benzylidenecyanoacetic acid ethyl ester, 7.2 g amidinoacetic acid isopropyl ester and 0.6 g sodium ethylate in 150 ml ethanol for four hours, 2,6-diamino-4-phenyl-1,4-dihydropyridine-3,5-dicarboxylic acid 3-ethyl ester 5-isopropyl ester of m.p. 170° is obtained.

Yield: 54% of theory.

EXAMPLE 22

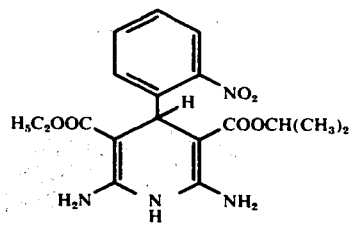

Upon heating a solution of 12.3 g 2-nitrobenzylidenecyanoacetic acid ethyl ester, 7.2 g amidinoacetic acid isopropyl ester and 0.6 g sodium ethylate in 150 ml ethanol for four hours, 2,6-diamino-4-(2-nitrophenyl)-1,4-dihydropyridine-3,5-dicarboxylic acid-3-isopropyl ester 5-ethyl ester of m.p. 110° C is obtained.

Yield: 54% of theory.

EXAMPLE 23

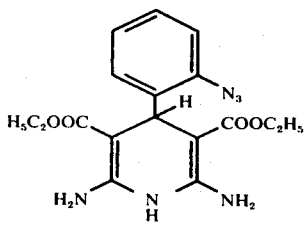

Upon heating a solution of 7.3 g 2-azidobenzaldehyde and 13.0 g amidinoacetic acid ethyl ester in 150 ml ethanol for two hours, 2,6-diamino-4-(2-azidophenyl)-1,4-dihydropyridine-3,5-dicarboxylic acid diethyl ester of m.p. 250° C (ethanol) is obtained.

Yield: 46% of theory.

EXAMPLE 24

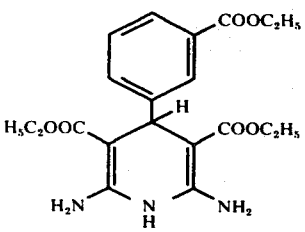

Upon boiling a solution of 8.9 g 3-carbethoxybenzaldehyde and 13.0 g amidinoacetic acid ethyl ester in 100 ml ethanol for two hours, 2,6-diamino-4-(3-carbethoxyphenyl)-1,4-dihydropyridine-3,5-dicarboxylic acid diethyl ester of m.p. 191° C (ethanol) is obtained.

Yield: 32% of theory.

What is claimed is:

1. A pharmaceutical composition useful for effecting coronary vessel dilation and treating hypertension in humans and animals which comprises a coronary vessel dilating amount or an antihypertensive amount of a compound of the formula:

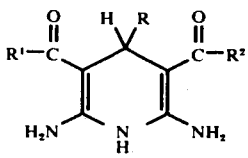

wherein
R is quinolyl or isoquinolyl, unsubstituted or substituted by one or two members selected from the group consisting of lower alkyl, lower alkoxy and halogeno; and
each of $R^1$ and $R^2$, taken independently of the other, is lower alkoxy, lower alkoxy(lower alkoxy), alkenyloxy of 2 to 4 carbon atoms, alkynyloxy of 2 to 4 carbon atoms, amino, lower alkylamino or di(-lower alkyl)amino.

in combination with a pharmaceutically acceptable non-toxic inert diluent or carrier.

2. A composition according to claim 1 wherein R is unsubstituted quinolyl or isoquinolyl, and $R^1$ and $R^2$ are lower alkoxy.

3. A composition according to claim 1 wherein said compound is 2,6-diamino-4-(quinol-4-yl)-1,4-dihydropyridine3,5-dicarboxylic acid diethyl ester.

4. A method of effecting coronary vessel dilation in humans and animals which comprises administering to such human or animal a coronary vessel dilating amount of a compound of the formula:

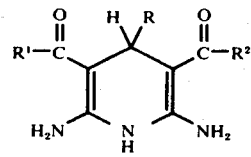

wherein
R is quinolyl or isoquinolyl, unsubstituted or substituted by one or two members selected from the group consisting of lower alkyl, lower alkoxy and halogeno; and
each of $R^1$ and $R^2$, taken independently of the other, is lower alkoxy, lower alkoxy(lower alkoxy), alkenyloxy of 2 to 4 carbon atoms, alkynyloxy of 2 to 4 carbon atoms, amino, lower alkylamino or di(-lower alkyl)amino.

5. A method according to claim 4 wherein R is unsubstituted quinolyl or isoquinolyl, and $R^1$ and $R^2$ are each lower alkoxy.

6. The method of claim 4 wherein said compound is 2,6-diamino-4-(quinol-4-yl)-1,4-dihydropyridine-3,5-dicarboxylic acid diethyl ester.

7. A method of treating hypertension in humans and animals which comprises administering to such human or animal an antihypertensive amount of a compound of the formula:

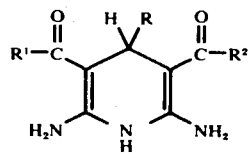

wherein
R is quinolyl or isoquinolyl, unsubstituted or substituted by one or two members selected from the group consisting of lower alkyl, lower alkoxy and halogeno; and
each of $R^1$ and $R^2$, taken independently of the other, is lower alkoxy, lower alkoxy(lower alkoxy), alkenyloxy of 2 to 4 carbon atoms, alkynyloxy of 2 to 4 carbon atoms, amino, lower alkylamino or di(-lower alkyl)amino.

8. A method according to claim 7 wherein R is unsubstituted quinolyl or isoquinolyl, and $R^1$ and $R^2$ are each lower alkoxy.

* * * * *